(12) United States Patent
Doyle et al.

(10) Patent No.: US 8,554,298 B2
(45) Date of Patent: Oct. 8, 2013

(54) MEDICAL VENTILATOR WITH INTEGRATED OXIMETER DATA

(75) Inventors: Peter Doyle, Vista, CA (US); Joseph Douglas Vandine, Manteca, CA (US); Warren Sanborn, Escondido, CA (US); Dan Graboi, Encinitas, CA (US)

(73) Assignee: Cividien LP, Mansfield, MA (US)

( * ) Notice: Subject to any disclaimer, the term of this patent is extended or adjusted under 35 U.S.C. 154(b) by 434 days.

(21) Appl. No.: 12/887,077

(22) Filed: Sep. 21, 2010

(65) Prior Publication Data

US 2012/0071729 A1    Mar. 22, 2012

(51) Int. Cl.
*A61B 5/1455* (2006.01)
*A61B 5/00* (2006.01)

(52) U.S. Cl.
USPC .......................... 600/323; 600/301; 600/333

(58) Field of Classification Search
USPC ......... 600/310, 324, 333, 340, 529, 538, 300, 600/301, 323; 128/203.12–207.18
See application file for complete search history.

(56) References Cited

U.S. PATENT DOCUMENTS

| | | | |
|---|---|---|---|
| 3,805,780 A | 4/1974 | Cramer et al. |
| 3,941,124 A | 3/1976 | Rodewald et al. |
| 4,056,098 A | 11/1977 | Michel et al. |
| 4,305,388 A | 12/1981 | Brisson |
| 4,340,044 A | 7/1982 | Levy et al. |
| 4,752,089 A | 6/1988 | Carter |
| 4,921,642 A | 5/1990 | LaTorraca |
| 4,939,647 A | 7/1990 | Clough et al. |
| 4,954,799 A | 9/1990 | Kumar |
| 4,971,052 A | 11/1990 | Edwards |
| 4,986,268 A | 1/1991 | Tehrani |
| 5,057,822 A | 10/1991 | Hoffman |
| 5,072,737 A | 12/1991 | Goulding |
| 5,094,235 A | 3/1992 | Westenskow et al. |
| 5,150,291 A | 9/1992 | Cummings et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,315,989 A | 5/1994 | Tobia |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |

(Continued)

FOREIGN PATENT DOCUMENTS

| | | |
|---|---|---|
| WO | WO04000114 | 12/2003 |
| WO | WO2007145948 | 12/2007 |

OTHER PUBLICATIONS

7200 Series Ventilator, Options, and Accessories: Operators Manual. Nellcor Puritan Bennett, Part No. 22300 A, Sep. 1990, pp. 1-196.

(Continued)

*Primary Examiner* — Eric Winakur
*Assistant Examiner* — Chu Chuan (JJ) Liu

(57) ABSTRACT

This disclosure describes systems and methods for managing the ventilation of a patient being ventilated by a medical ventilator. The disclosure describes a novel approach of displaying ventilator information integrated with oximeter information. The disclosure further describes a novel approach of alarming based on the integration of ventilator information with oximeter information.

17 Claims, 12 Drawing Sheets

(56) References Cited

U.S. PATENT DOCUMENTS

| | | |
|---|---|---|
| 5,343,857 A | 9/1994 | Schneider et al. |
| 5,351,522 A | 10/1994 | Lura |
| 5,357,946 A | 10/1994 | Kee et al. |
| 5,365,922 A | 11/1994 | Raemer |
| 5,368,019 A | 11/1994 | LaTorraca |
| 5,383,449 A | 1/1995 | Forare et al. |
| 5,385,142 A | 1/1995 | Brady et al. |
| 5,388,575 A | 2/1995 | Taube |
| 5,390,666 A | 2/1995 | Kimm et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,438,980 A | 8/1995 | Phillips |
| 5,443,075 A | 8/1995 | Holscher |
| 5,503,147 A | 4/1996 | Bertheau |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |
| 5,542,415 A | 8/1996 | Brady |
| 5,544,674 A | 8/1996 | Kelly |
| 5,549,106 A | 8/1996 | Gruenke et al. |
| 5,551,419 A | 9/1996 | Froehlich et al. |
| 5,596,984 A | 1/1997 | O'Mahoney et al. |
| 5,605,151 A | 2/1997 | Lynn |
| 5,623,923 A | 4/1997 | Bertheau et al. |
| 5,630,411 A | 5/1997 | Holscher |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,692,497 A | 12/1997 | Schnitzer et al. |
| 5,715,812 A | 2/1998 | Deighan et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,891,023 A | 4/1999 | Lynn |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,123,074 A | 9/2000 | Hete et al. |
| 6,135,106 A | 10/2000 | Dirks et al. |
| 6,142,150 A | 11/2000 | O'Mahoney |
| 6,148,814 A | 11/2000 | Clemmer et al. |
| 6,158,430 A | 12/2000 | Pfeiffer et al. |
| 6,158,432 A | 12/2000 | Biondi et al. |
| 6,159,147 A | 12/2000 | Lichter et al. |
| 6,161,539 A | 12/2000 | Winter |
| 6,220,245 B1 | 4/2001 | Takabayashi et al. |
| 6,223,064 B1 | 4/2001 | Lynn et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,342,039 B1 | 1/2002 | Lynn et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,371,114 B1 | 4/2002 | Schmidt et al. |
| 6,390,091 B1 | 5/2002 | Banner et al. |
| 6,412,483 B1 | 7/2002 | Jones et al. |
| 6,439,229 B1 | 8/2002 | Du et al. |
| 6,467,478 B1 | 10/2002 | Merrick et al. |
| 6,512,938 B2 | 1/2003 | Claure et al. |
| 6,532,958 B1 | 3/2003 | Buan et al. |
| 6,532,959 B1 | 3/2003 | Berthon-Jones |
| 6,532,960 B1 | 3/2003 | Yurko |
| 6,536,429 B1 | 3/2003 | Pavlov et al. |
| 6,543,449 B1 | 4/2003 | Woodring et al. |
| 6,546,930 B1 | 4/2003 | Emerson et al. |
| 6,553,991 B1 | 4/2003 | Isaza |
| 6,557,553 B1 | 5/2003 | Borrello |
| 6,561,187 B2 | 5/2003 | Schmidt et al. |
| 6,571,795 B2 | 6/2003 | Bourdon |
| 6,602,191 B2 | 8/2003 | Quy |
| 6,609,016 B1 | 8/2003 | Lynn |
| 6,622,726 B1 | 9/2003 | Du |
| 6,640,806 B2 | 11/2003 | Yurko |
| 6,644,310 B1 | 11/2003 | Delache et al. |
| 6,644,312 B2 | 11/2003 | Berthon-Jones et al. |
| 6,665,385 B2 | 12/2003 | Rogers et al. |
| 6,668,824 B1 | 12/2003 | Isaza et al. |
| 6,671,529 B2 | 12/2003 | Claure et al. |
| 6,675,801 B2 | 1/2004 | Wallace et al. |
| 6,688,307 B2 | 2/2004 | Berthon-Jones |
| 6,718,974 B1 | 4/2004 | Moberg |
| 6,723,055 B2 | 4/2004 | Hoffman |
| 6,725,447 B1 | 4/2004 | Gilman et al. |
| 6,739,337 B2 | 5/2004 | Isaza |
| 6,748,252 B2 | 6/2004 | Lynn et al. |
| 6,752,151 B2 | 6/2004 | Hill |
| 6,758,216 B1 | 7/2004 | Berthon-Jones et al. |
| 6,760,608 B2 | 7/2004 | Lynn |
| 6,761,165 B2 | 7/2004 | Strickland |
| 6,761,167 B1 | 7/2004 | Nadjafizadeh et al. |
| 6,761,168 B1 | 7/2004 | Nadjafizadeh et al. |
| 6,796,305 B1 | 9/2004 | Banner et al. |
| 6,814,074 B1 | 11/2004 | Nadjafizadeh et al. |
| 6,820,618 B2 | 11/2004 | Banner et al. |
| 6,837,242 B2 | 1/2005 | Younes |
| 6,866,040 B1 | 3/2005 | Bourdon |
| 6,868,346 B2 | 3/2005 | Larson et al. |
| 6,960,854 B2 | 11/2005 | Nadjafizadeh et al. |
| 7,008,380 B1 | 3/2006 | Rees et al. |
| 7,036,504 B2 | 5/2006 | Wallace et al. |
| 7,040,315 B1 * | 5/2006 | Stromberg ............... 128/203.14 |
| 7,066,173 B2 | 6/2006 | Banner et al. |
| 7,077,131 B2 | 7/2006 | Hansen |
| 7,081,095 B2 | 7/2006 | Lynn et al. |
| RE39,225 E | 8/2006 | Isaza et al. |
| 7,089,936 B2 | 8/2006 | Madaus et al. |
| 7,092,376 B2 | 8/2006 | Schuman |
| 7,092,757 B2 | 8/2006 | Larson et al. |
| 7,100,609 B2 | 9/2006 | Berthon-Jones et al. |
| 7,117,438 B2 | 10/2006 | Wallace et al. |
| 7,152,598 B2 | 12/2006 | Morris et al. |
| 7,210,478 B2 | 5/2007 | Banner et al. |
| 7,229,430 B2 | 6/2007 | Hickle et al. |
| 7,267,122 B2 | 9/2007 | Hill |
| 7,270,126 B2 | 9/2007 | Wallace et al. |
| 7,275,540 B2 | 10/2007 | Bolam et al. |
| 7,296,573 B2 | 11/2007 | Estes et al. |

(56) References Cited

U.S. PATENT DOCUMENTS

| | | |
|---|---|---|
| 7,297,119 B2 | 11/2007 | Westbrook et al. |
| 7,315,535 B2 | 1/2008 | Schuman |
| 7,331,343 B2 | 2/2008 | Schmidt et al. |
| 7,353,824 B1 | 4/2008 | Forsyth et al. |
| 7,369,757 B2 | 5/2008 | Farbarik |
| 7,370,650 B2 | 5/2008 | Nadjafizadeh et al. |
| 7,398,115 B2 | 7/2008 | Lynn |
| 7,406,870 B2 | 8/2008 | Seto |
| 7,428,902 B2 | 9/2008 | Du et al. |
| 7,448,381 B2 | 11/2008 | Sasaki et al. |
| 7,455,583 B2 | 11/2008 | Taya |
| 7,460,959 B2 | 12/2008 | Jafari |
| 7,487,773 B2 | 2/2009 | Li |
| 7,509,957 B2 | 3/2009 | Duquette et al. |
| 7,590,551 B2 | 9/2009 | Auer |
| 7,654,802 B2 | 2/2010 | Crawford, Jr. et al. |
| 7,694,677 B2 | 4/2010 | Tang |
| 7,698,156 B2 | 4/2010 | Martucci et al. |
| 7,715,387 B2 | 5/2010 | Schuman |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,414,488 B2 * | 4/2013 | Colman et al. ............... 600/301 |
| 2002/0133061 A1 | 9/2002 | Manetta |
| 2002/0185126 A1 | 12/2002 | Krebs |
| 2003/0158466 A1 | 8/2003 | Lynn et al. |
| 2003/0221689 A1 | 12/2003 | Berthon-Jones |
| 2005/0039748 A1 | 2/2005 | Andrieux |
| 2005/0109340 A1 | 5/2005 | Tehrani |
| 2005/0133027 A1 | 6/2005 | Elaz et al. |
| 2005/0139212 A1 | 6/2005 | Bourdon |
| 2005/0172965 A1 | 8/2005 | Thulin |
| 2006/0112959 A1 | 6/2006 | Mechlenburg et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0189880 A1 | 8/2006 | Lynn et al. |
| 2006/0195041 A1 | 8/2006 | Lynn et al. |
| 2006/0235324 A1 | 10/2006 | Lynn |
| 2006/0241708 A1 | 10/2006 | Boute |
| 2006/0264762 A1 | 11/2006 | Starr |
| 2006/0272642 A1 | 12/2006 | Chalvignac |
| 2007/0000494 A1 | 1/2007 | Banner et al. |
| 2007/0016441 A1 | 1/2007 | Stroup |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0072541 A1 | 3/2007 | Daniels, II et al. |
| 2007/0077200 A1 | 4/2007 | Baker |
| 2007/0093721 A1 | 4/2007 | Lynn et al. |
| 2007/0129647 A1 | 6/2007 | Lynn |
| 2007/0149860 A1 | 6/2007 | Lynn et al. |
| 2007/0157931 A1 | 7/2007 | Parker et al. |
| 2007/0163579 A1 | 7/2007 | Li et al. |
| 2007/0185390 A1 | 8/2007 | Perkins et al. |
| 2007/0191688 A1 | 8/2007 | Lynn |
| 2007/0191697 A1 | 8/2007 | Lynn et al. |
| 2007/0215154 A1 | 9/2007 | Borrello |
| 2007/0227537 A1 | 10/2007 | Bemister et al. |
| 2007/0272241 A1 | 11/2007 | Sanborn et al. |
| 2007/0277823 A1 | 12/2007 | Al-Ali et al. |
| 2007/0284361 A1 | 12/2007 | Nadjafizadeh et al. |
| 2008/0000479 A1 | 1/2008 | Elaz et al. |
| 2008/0053441 A1 | 3/2008 | Gottlib et al. |
| 2008/0066752 A1 | 3/2008 | Baker et al. |
| 2008/0066753 A1 | 3/2008 | Martin et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0110460 A1 | 5/2008 | Elaz et al. |
| 2008/0178880 A1 | 7/2008 | Christopher et al. |
| 2008/0178882 A1 | 7/2008 | Christopher et al. |
| 2008/0190430 A1 * | 8/2008 | Melker et al. ............ 128/204.23 |
| 2008/0200775 A1 | 8/2008 | Lynn |
| 2008/0200819 A1 | 8/2008 | Lynn et al. |
| 2008/0251079 A1 | 10/2008 | Richey |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |

(56) References Cited

U.S. PATENT DOCUMENTS

| | | |
|---|---|---|
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |

OTHER PUBLICATIONS

7200 Ventilatory System: Addendum/Errata. Nellcor Puritan Bennett, Part No. 4-023576-00, Rev. A, Apr. 1998, pp. 1-32.

800 Operators and Technical Reference Manual. Series Ventilator System, Nellcor Puritan Bennett, Part No. 4-070088-00, Rev. L, Aug. 2010, pp. 1-476.

840 Operators and Technical Reference Manual. Ventilator System, Nellcor Puritan Bennett, Part No. 4-075609-00, Rev. G, Oct. 2006, pp. 1-424.

* cited by examiner

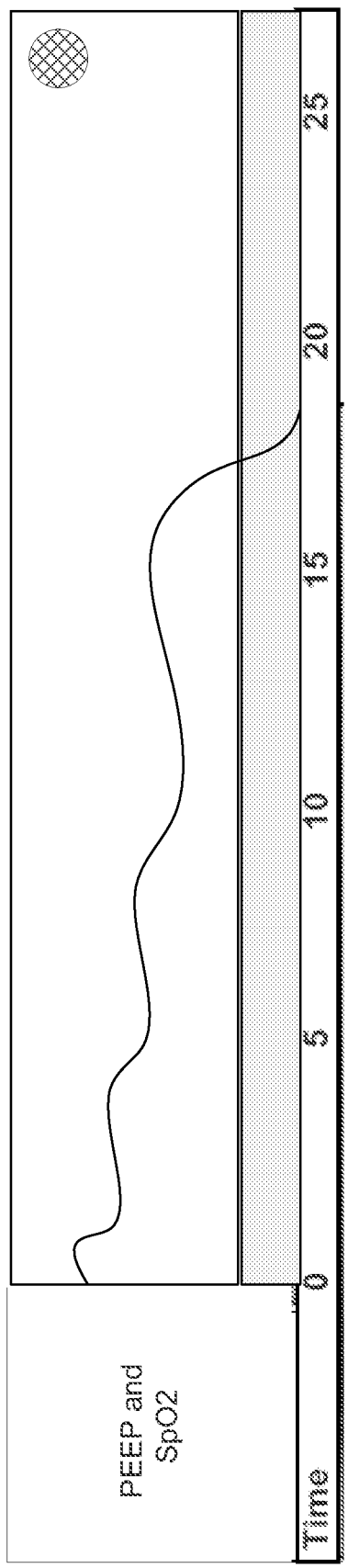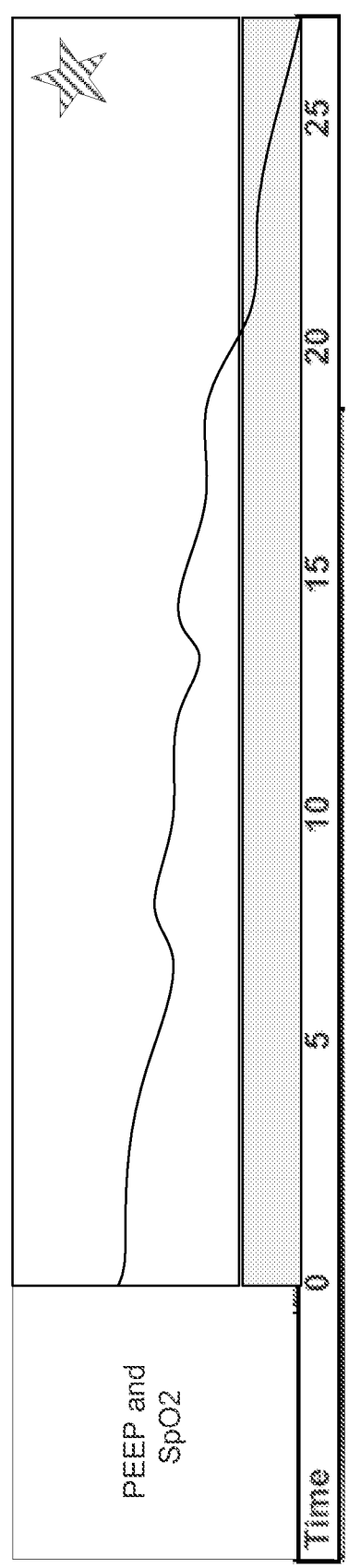
FIG. 9
FIG. 10

MEDICAL VENTILATOR WITH INTEGRATED OXIMETER DATA

BACKGROUND

Medical ventilator systems have been long used to provide supplemental oxygen support to patients. These ventilators typically comprise a source of pressurized oxygen which is fluidly connected to the patient through a conduit. Some ventilator systems monitor the patient during ventilation. In some systems, the pulse arterial oxygen saturation ($SpO_2$) is monitored via a pulse oximeter attached to the patient.

A pulse oximeter includes a light sensor that is placed at a site on a patient, usually a fingertip, toe, forehead or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

Some of previously known medical ventilators attempt to automate the adjustment of fractional inspired oxygen ($FiO_2$) as a function of the patient's $SpO_2$. While these previously known automated ventilation systems utilize the oximeter readings for improving ventilation, patient care could be improved by further coordinating the operation of the two devices, particularly by integrating the analysis, storage and display of particular aspects of oximeter data and respiratory data.

SUMMARY

This disclosure describes systems and methods for managing the ventilation of a patient being ventilated by a medical ventilator. The disclosure describes a novel approach of displaying ventilator information integrated with oximeter information. The disclosure further describes a novel approach of alarming based on the integration of ventilator information with oximeter information.

In part, this disclosure describes a method for managing the ventilation of a patient being ventilated by a medical ventilator. The method includes:
a) monitoring a patient during ventilation with an oximeter;
b) monitoring an oxygen saturation level of blood in the patient during ventilation;
c) monitoring a PEEP level of the patient;
d) graphing the oxygen saturation level of the blood in the patient as a function of the PEEP level versus time; and
e) displaying a graph of the function versus time.

The disclosure also describes another method for managing the ventilation of a patient being ventilated by a medical ventilator. The method includes:
a) monitoring a patient during ventilation with an oximeter;
b) monitoring an oxygen saturation level of blood in the patient during ventilation based on readings from the oximeter;
c) monitoring a PEEP level of the patient;
d) graphing the oxygen saturation level of the blood in the patient versus time;
e) graphing the PEEP level of the patient versus time; and
f) displaying both the oxygen saturation level of the blood in the patient versus time and the PEEP level of the patient versus time on one graph, The disclosure further describes another method for managing the ventilation of a patient being ventilated by a medical ventilator. The method includes:
a) monitoring a patient during ventilation with an oximeter;
b) monitoring an oxygen saturation level of blood in the patient during ventilation based on readings from the oximeter;
c) monitoring the PEEP of the patient;
d) monitoring the fractional inspired oxygen level of the patient;
e) graphing the oxygen saturation level of the blood in the patient versus time;
f) graphing the PEEP level of the patient versus time;
g) graphing the fractional inspired oxygen level of the patient versus time; and
h) displaying the oxygen saturation level of the blood in the patient versus time, the fractional inspired oxygen level of the patient versus time, and the PEEP level of the patient versus time on one graph.

Additionally, the disclosure also describes a computer-readable medium having computer-executable instructions for performing a method for managing the ventilation of a patient being ventilated by a medical ventilator. The method includes:
a) repeatedly monitoring a patient with an oximeter during ventilation;
b) repeatedly monitoring an oxygen saturation level of blood in the patient during ventilation;
c) repeatedly monitoring a PEEP level of the patient;
d) repeatedly graphing the oxygen saturation level of the blood in the patient in a mathematical relation to the PEEP level versus time; and
e) repeatedly displaying a graph of the mathematical relationship versus time.

Further, the disclosure also describes a medical ventilator system. The medical ventilator system includes means for repeatedly monitoring a patient during ventilation with an oximeter, means for repeatedly monitoring an oxygen saturation level of blood in the patient during ventilation, means for repeatedly monitoring a PEEP level of the patient, means for repeatedly graphing the oxygen saturation level of the blood in the patient in a mathematical relation to the PEEP level versus time, and means for repeatedly displaying a graph of the mathematical relationship versus time.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiment systems and methods described below and are not meant to limit the scope of the invention in any manner, which scope shall be based on the claims appended hereto.

FIG. 9 illustrates an embodiment of a graph of a function of $SpO_2$ and PEEP of a patient on a medical ventilator versus time as displayed on a display screen.

FIG. 10 illustrates an embodiment of a graph of a function of $SpO_2$ and PEEP of a patient on a medical ventilator versus time as displayed on a display screen.

DETAILED DESCRIPTION

Figure 1:
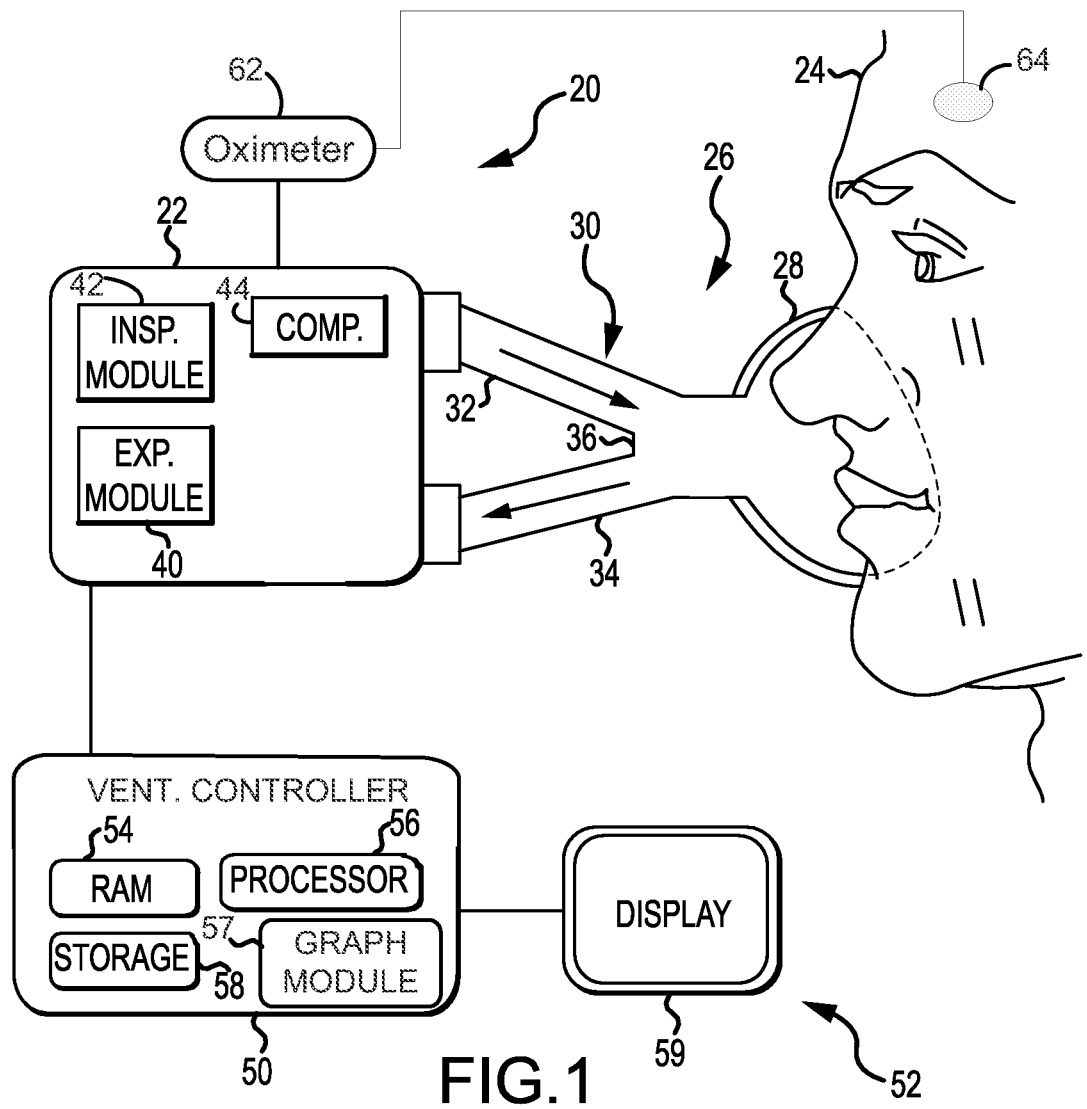
FIG. 1 illustrates an embodiment of a ventilator and oximeter connected to a human patient.

Although the techniques introduced above and discussed in detail below may be implemented for a variety of medical devices, the present disclosure will discuss the implementation of these techniques in the context of a medical ventilator and oximeter for use in providing ventilation support to a human patient. The reader will understand that the technology described in the context of a medical ventilator and oximeter for human patients could be adapted for use with other systems and purposes, such as treating non-human patients.

Medical ventilators are used to provide a breathing gas to a patient who may otherwise be unable to breathe sufficiently. In modern medical facilities, pressurized air and oxygen sources are often available from wall outlets. However, ventilators may also provide pressure regulating valves (or regulators) connected to localized sources of pressurized air and pressurized oxygen. Internal to the ventilator are regulating valves that function to regulate flow so that respiratory gas having a desired concentration of oxygen is supplied to the patient at desired pressures and rates. Ventilators capable of operating independently of external sources of pressurized air are also available.

While operating a ventilator, it is desirable to control the percentage of oxygen in the gas supplied by the ventilator to the patient. Further, it is desirable to monitor the oxygen saturation level of blood ($SpO_2$ level) of a patient. Accordingly, medical care facilities typically have oximeters for non-invasively determining the $SpO_2$ level of a patient.

Although ventilators and oximeters are often used on the same patient, ventilators typically display data based solely on respiratory data monitored by the ventilator. Further, oximeters typically display data based solely on the oximeter readings. However, it is desirable to display information that incorporates oximeter data with ventilator data for the patient, ventilator operator, and/or medical caregiver.

The present disclosure describes trended $SpO_2$ data that is graphically depicted on a display as a function of a Positive End-Expiratory Pressure (PEEP) and/or other respiratory parameters such as $FiO_2$. PEEP is the pressure exerted at the end of expiration to oppose passive emptying of the lung and to keep the airway pressure above the atmospheric pressure. By displaying the combination of $SpO_2$ and PEEP, a significantly clearer picture of the time-based cause and effect of PEEP on $SpO_2$ can be better inferred. This clearer picture allows a clinician to more appropriately adjust PEEP and/or oxygen levels.

Those skilled in the art will recognize that the methods and systems of the present disclosure may be implemented in many ways and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known ways for carrying out the described features and functions and interfaces, and those variations and modifications that may be made to the hardware or software or firmware components described herein as would be understood by those skilled in the art now and hereafter.

FIG. 1 illustrates an embodiment of a ventilator 20 connected to a human patient 24. Ventilator 20 includes a pneumatic system 22 (also referred to as a pressure generating system 22) for circulating breathing gases to and from patient 24 via the ventilation tubing system 26, which couples the patient 24 to the pneumatic system 22 via physical patient interface 28 and ventilator circuit 30. Ventilator 20 also includes an oximeter 62 for determining the $SpO_2$ of patient 24, which is operatively coupled to the ventilator 20 during ventilation.

Ventilator circuit 30 could be a two-limb or one-limb circuit 30 for carrying gas to and from the patient 24. In a two-limb embodiment as shown, a wye fitting 36 may be provided as shown to couple the patient interface 28 to the inspiratory limb 32 and the expiratory limb 34 of the circuit 30.

The present description contemplates that the patient interface 28 may be invasive or non-invasive, and of any configuration suitable for communicating a flow of breathing gas from the patient circuit 30 to an airway of the patient 24. Examples of suitable patient interface 28 devices include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an expiratory module 40 coupled with an expiratory limb 34 and an inspiratory module 42 coupled with an inspiratory limb 32. Compressor 44 or another source or sources of pressurized gas (e.g., pressured air and/or oxygen) is controlled through the use of one or more gas regulators. The pneumatic system 22 may include a variety of other components, including sources for pressurized air and/or oxygen, mixing modules, valves, sensors, tubing, filters, etc.

The oximeter 62 is connected to a patient oximeter sensor 64. As illustrated, in an embodiment, the oximeter 62 is a completely separate and independent component from the ventilator 20. In an alternative embodiment, the oximeter 62 is part of the ventilator system or the pneumatic system 22.

The oximeter 62 determines an oxygen gas saturation level of blood in the patient based on the patient readings taken by the pulse oximeter sensor 64 during ventilation of patient 24 by the ventilator 20. The oximeter sends the measured oxygen saturation level of the blood of patient 24 to a controller 50. The controller 50 may be any individual controller or combination of controllers within ventilator 20 or operatively coupled to ventilator 20. In one embodiment, the controller 50 includes a $SpO_2$ controller, PEEP controller and/or $FiO_2$ controller. Controller 50 monitors the PEEP of patient 24. In one embodiment, controller 50 sends a graph plotting the $SpO_2$ and PEEP of patient 24 in two separate lines versus time on the same graph to display 59. In another embodiment, controller 50 sends the necessary data to the display 59 for displaying a graph plotting a function of $SpO_2$ and PEEP versus time.

In an additional embodiment, controller 50 monitors the fractional inspired oxygen ($FiO_2$) delivered to patient 24. In one embodiment, controller 50 sends the necessary data to display 59 for displaying a graph plotting $SpO_2$, $FiO_2$ and PEEP of patient 24 in three separate lines versus time on the same graph. In another embodiment, controller 50 sends the necessary data to display 59 for displaying a graph plotting a function of $FiO_2$, $SpO_2$ and PEEP versus time on a graph.

In this embodiment, the function of $SpO_2$ and PEEP or $FiO_2$, $SpO_2$ and PEEP may be the multiplication, addition, subtraction, ratio and/or any other mathematical relationship between the separate readings. This function is then plotted on a graph versus time. In an embodiment, controller 50 sends the necessary data to the display 59 for displaying a graph plotting the blood gas oxygen saturation level along with the fractional inspired oxygen concentration and PEEP to graphically depict the relationship between $FiO_2$, $SpO_2$ and PEEP.

In one embodiment, the graph is displayed on an oximeter display. In another embodiment, the graph is displayed on a ventilator display 59.

In another embodiment, the graph may display upper and/or lower preset thresholds for the plotted line or lines. As used herein, the term "preset" refers to any parameter that is calculated by the operator, entered by the operator, set during configuration, or selected by the operator. In this embodiment, the graph may designate with lines, colors, and/or shapes a preset threshold for the plotted line or lines. The preset threshold marker provides the patient, ventilator operator, and/or medical caregiver with a quick and easy way to check the status of the patient. Further, the patient, ventilator operator, and/or medical caregiver can determine with one glance the severity of a preset threshold breach. The severity of the breach is determined by the amount by which the parameter exceeds the preset threshold, the magnitude of the breach and the duration of the breach, which are fully visible in this embodiment to the patient, ventilator operator, and/or medical caregiver on the displayed graph. Further, the graph illustrates the relationship between $SpO_2$ and PEEP or $SpO_2$ and $FiO_2$ at a glance providing the operator with additional useful information for operating the ventilator. In another embodiment, the graph illustrates the relationship between $SpO_2$, $FiO_2$, and PEEP at a glance providing the operator with additional useful information for managing the ventilator.

In one embodiment, as illustrated in FIG. 1, the plotting of the data is performed by a graph module 57 in controller 50. The graph module 57 interprets the $SpO_2$, and PEEP data, and/or $FiO_2$ data and converts this information into the form necessary for graphing the $SpO_2$ and PEEP and/or $FiO_2$ or a function of $SpO_2$ and PEEP versus time and/or a function of $SpO_2$, $FiO_2$, and PEEP versus time and for displaying the determined graph on a display screen. In an alternative embodiment, the graph module 57 is part of the oximeter 62. In another embodiment, the graph module 57 includes a processor and is a separate and independent component from the controller 50.

In a further embodiment, controller 50 issues an alarm based on the graphed information to notify the operator, patient, and/or medical caregiver that the patient requires assistance or a change in ventilator parameters and/or features is desirable. For example, if the function of $SpO_2$ and PEEP and/or $FiO_2$ falls below or above a preset threshold in a patient, the controller 50 may execute an alarm. The alarm may be any visual and/or audio cue supplemental to the graphed information that notifies the patient, operator, and/or medical care giver of a preset threshold breach. In another example, controller 50 determines if the PEEP of patient 24 drops before a drop in $SpO_2$, such as could occur in response to a clinician lowering PEEP. In this embodiment, if controller 50 determines that PEEP dropped before a drop in $SpO_2$, controller 50 executes a $2^{nd}$ type $SpO_2$ alarm. As used herein, a "$2^{nd}$ type $SpO_2$ alarm" is any suitable audio and/or visual warning supplemental to the graph information that notifies the patient, operator, and/or medical care giver of a preset threshold breach with a drop in PEEP prior to a drop in $SpO_2$. As used herein, a "$3^{rd}$ type $SpO_2$ alarm" is any suitable audio and/or visual warning supplemental to the graph information that notifies the patient, operator, and/or medical care giver of a preset threshold breach with a drop in $FiO_2$ prior to a drop in $SpO_2$. In yet another example, the controller 50 determines if $SpO_2$ drops independently of a change in PEEP and/or $FiO_2$. If controller 50 determines a drop in $SpO_2$ independent of a change in PEEP and/or $FiO_2$, the controller 50 executes a first type oxygen saturation or $1^{st}$ type $SpO_2$ alarm. As used herein, a "$1^{st}$ type $SpO_2$ alarm" is any suitable audio and/or visual warning supplemental to the graph information that notifies the patient, operator, and/or medical care giver of a preset threshold breach with a drop in $SpO_2$ independent of a change in PEEP and/or $FiO_2$.

In another embodiment, the ventilator may alarm if the plotted parameter exceeds the preset threshold. The alarm may include a visual cue and/or an audio cue. Further, the alarm may offer different levels or degrees of visual cues and/or audio cues depending upon the severity of the preset threshold breach.

Controller 50 is operatively coupled with pneumatic system 22, signal measurement and acquisition systems, and an operator interface 52, which may be provided to enable an operator to interact with the ventilator 20 (e.g., change ventilator settings, select operational modes, view monitored parameters, etc.). In one embodiment, controller 50 is operatively coupled with a $SpO_2$ controller, PEEP controller, and/or $FiO_2$ controller. Controller 50 may include memory 54, one or more processors 56, storage 58, and/or other components of the type commonly found in command and control computing devices.

The memory 54 is non-transitory computer-readable storage media that stores software that is executed by the processor 56 and which controls the operation of the ventilator 20. In an embodiment, the memory 54 comprises one or more solid-state storage devices such as flash memory chips. In an alternative embodiment, the memory 54 may be mass storage connected to the processor 56 through a mass storage controller (not shown) and a communications bus (not shown). Although the description of non-transitory computer-readable media contained herein refers to a solid-state storage, it should be appreciated by those skilled in the art that non-transitory computer-readable storage media can be any available media that can be accessed by the processor 56. Non-transitory computer-readable storage media includes volatile and non-volatile, removable and non-removable media implemented in any method or technology for storage of information such as computer-readable instructions, data structures, program modules or other data. Non-transitory computer-readable storage media includes, but is not limited to, RAM, ROM, EPROM, EEPROM, flash memory or other solid state memory technology, CD-ROM, DVD, or other optical storage, magnetic disk storage or other magnetic storage devices, or any other medium which can be used to store the desired information and which can be accessed by the processor 56.

The controller 50 issues commands to pneumatic system 22 in order to control the breathing assistance provided to the patient 24 by the ventilator 20. The specific commands may be based on inputs received from patient 24, pneumatic system 22 and sensors, operator interface 52 and/or other components of the ventilator 20.

In the depicted example, operator interface 52 includes a display 59 that is touch-sensitive, enabling the display 59 to serve both as an input user interface and an output device. The display 59 can display any type of ventilation information, such as sensor readings, parameters, commands, alarms, warnings, and smart prompts (i.e., ventilator determined operator suggestions). In this embodiment, display 59 further displays oximeter and ventilator information, such as a graph of $SpO_2$ in relation to PEEP versus time. In an alternative embodiment, an oximeter display or monitor displays oximeter and ventilator information, such as a graph of $SpO_2$ in relation to PEEP versus time.

In another embodiment, display 59 further displays oximeter and ventilator information, such as a graph of $SpO_2$ in relation to PEEP and $FiO_2$ versus time. In an alternative embodiment, an oximeter display or monitor displays oximeter and ventilator information, such as a graph of $SpO_2$ in relation to PEEP and $FiO_2$ versus time.

Figure 2A:
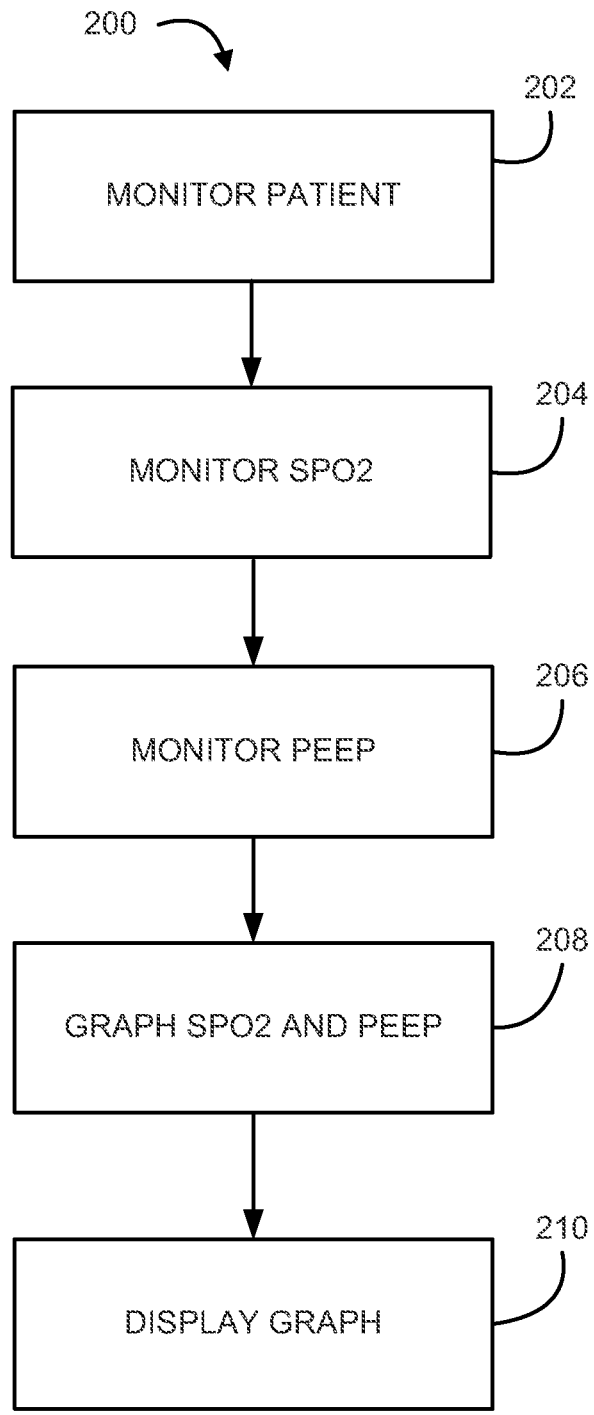
FIG. 2A illustrates an embodiment of a method for managing the ventilation of a patient being ventilated by a medical ventilator.
Figure 2B:
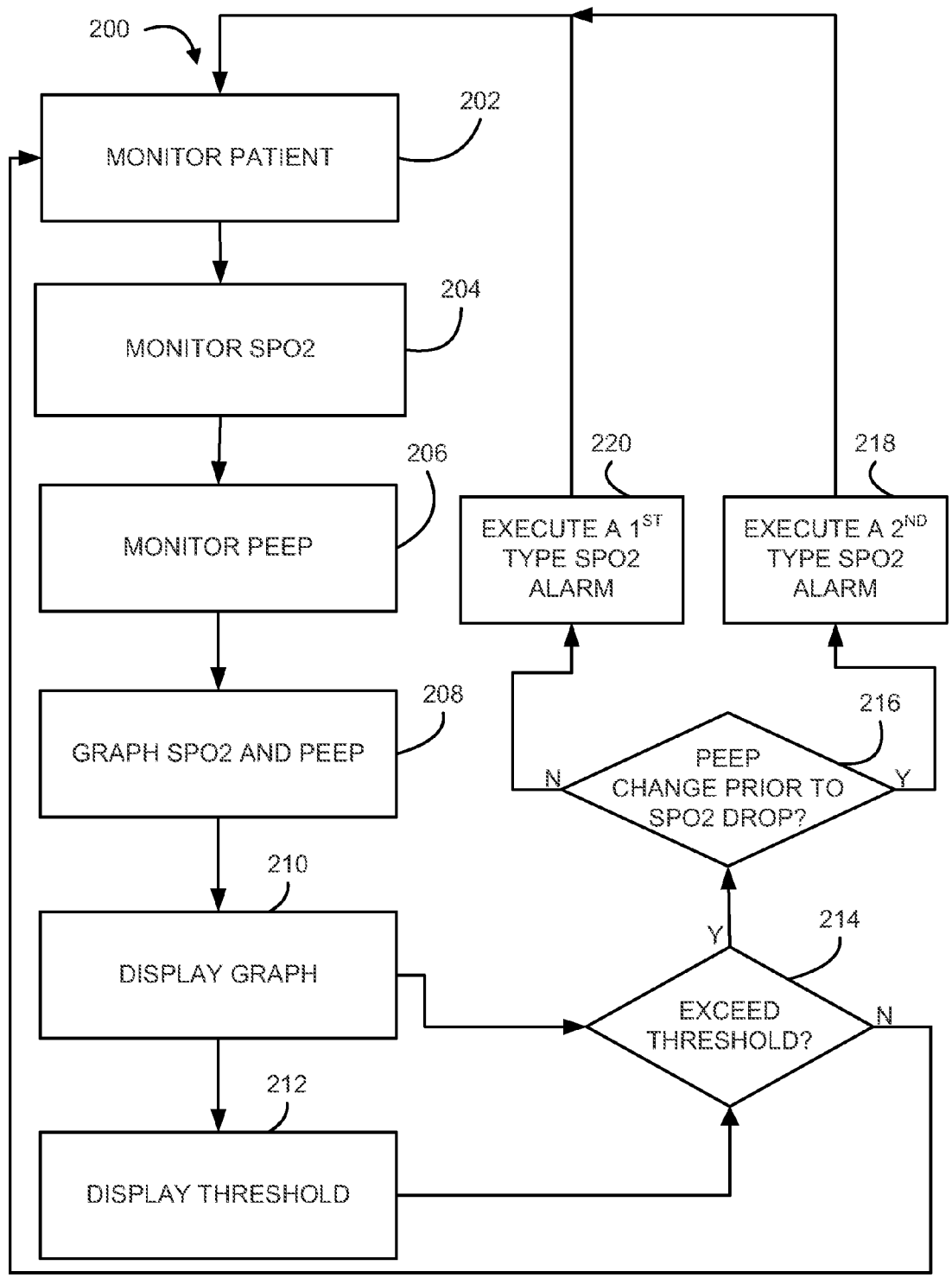
FIG. 2B illustrates an embodiment of a method for managing the ventilation of a patient being ventilated by a medical ventilator.

As illustrated in FIGS. 2A and 2B, an embodiment of a method 200 for managing the ventilation of a patient being ventilated by a medical ventilator is shown. Method 200 performs a patient monitoring operation 202. The patient monitoring operation 202 utilizes an oximeter to monitor the status of a patient during ventilation. The oximeter is operatively coupled to the controller of the ventilation system.

Next, method 200 performs a $SpO_2$ monitoring operation 204. The $SpO_2$ monitoring operation 204 determines the $SpO_2$ of the patient from patient data gathered by patient monitoring operation 202. The $SpO_2$ monitoring operation 204 can be performed by the oximeter and/or the ventilator by utilizing oximeter sensor readings to monitor the $SpO_2$ of the patient.

Further, method 200 performs a PEEP monitoring operation 206. The PEEP monitoring operation 206 monitors the PEEP of the patient during ventilation. The PEEP monitoring operation 206 may monitor the PEEP of the patient with one or more flow and/or pressure sensors depending on the configuration of the ventilator. The reading from the flow and/or pressure sensors may be utilized to monitor the PEEP of the patient.

Method 200 performs a graphing operation 208. The graphing operation 208 graphs $SpO_2$ and PEEP versus time. In one embodiment, graphing operation 208 graphs PEEP and $SpO_2$ as separate lines on one graph. In an alternative embodiment, graphing operation 208 calculates a function of PEEP and $SpO_2$ and graphs this number as one line versus time. The function of $SpO_2$ and PEEP may be the multiplication, addition, subtraction, ratio and/or any other mathematical relationship between of the separate readings.

In one embodiment, the graphing operation 208 is performed by a controller. Further, the controller may include a graphing module for receiving and interpreting the PEEP and $SpO_2$ data to correctly graph this data versus time. The graphing operation 208 converts the PEEP and $SpO_2$ data into graphable information and displayable information.

Method 200 also performs a display operation 210. Display operation 210 displays the graph created by graphing operation 208. The displaying operation 210 may display the graph on a display in the oximeter and/or ventilator. As illustrated in FIGS. 6 through 11, an embodiment of a graph of a function of $SpO_2$ and PEEP or separate $SpO_2$ and PEEP readings of a patient on a medical ventilator as displayed on a display screen is shown.

In one embodiment, as illustrated in FIG. 2B, method 200 further performs a preset threshold display operation 212. The preset threshold display operation 212 displays at least one preset threshold on the graph displayed by display operation 210. The preset threshold provides the patient, operator, and/or medical care giver with a quick reference point to determine the status of the patient during ventilation. In an embodiment, preset threshold display operation 212 displays an upper and a lower preset threshold limit on the graphed function of $SpO_2$ and PEEP or each reading individually. Preset threshold display operation 212 may depict a preset threshold with color, symbols, lines, light, and/or text. The preset threshold may be preset by the operator, configured into the ventilator based on the ventilator settings, and/or selected by the operator.

As illustrated in FIG. 2B, method 200 may further perform a preset threshold determination operation 214. The preset threshold determination operation 214 determines if PEEP, $SpO_2$, and/or a function of PEEP and $SpO_2$ exceeds a preset threshold. If preset threshold determination operation 214 determines that PEEP, $SpO_2$, and/or a function of PEEP and $SpO_2$ exceeds a preset threshold, preset threshold determination operation 214 has method 200 perform PEEP determination operation 216. If preset threshold determination operation 214 determines that PEEP, $SpO_2$, and/or a function of PEEP and $SpO_2$ do not exceed a preset threshold, preset threshold determination operation 214 has method 200 perform patient monitoring operation 202 again.

As illustrated in FIG. 2B, method 200 may further perform a PEEP determination operation 216. The PEEP determination operation 216 determines if PEEP changes prior to a $SpO_2$ drop after preset threshold determination operation 214 determines that a preset threshold had been exceeded. If PEEP determination operation 216 determines that PEEP changed prior to a $SpO_2$ drop, PEEP determination operation 216 has method 200 perform a $2^{nd}$ type $SpO_2$ alarm operation 218. If PEEP determination operation 216 determines that $SpO_2$ dropped independently of a change in PEEP, PEEP determination operation 216 has method 200 perform a $1^{st}$ type $SpO_2$ alarm operation 220.

As illustrated in FIG. 2B, method 200 may perform a $2^{nd}$ type $SpO_2$ alarm operation 218. Second type $SpO_2$ alarm operation 218 executes a specific alarm that notifies the operator that a preset threshold was exceeded during which PEEP changed prior to a drop in $SpO_2$. The $2^{nd}$ type $SpO_2$ alarm may be any visual and/or audio cue.

As illustrated in FIG. 2B, method 200 may perform $1^{st}$ type $SpO_2$ alarm operation 220. First type $SpO_2$ alarm operation 220 executes a specific alarm that notifies the operator that a preset threshold was exceeded during which PEEP did not change prior to a drop in $SpO_2$. The $1^{st}$ type $SpO_2$ alarm may be any visual and/or audio cue.

After performing the $2^{nd}$ type $SpO_2$ alarm operation 218 or the $1^{st}$ type $SpO_2$ alarm operation 220, method 200 performs patient monitoring operation 202 again.

In an additional embodiment, method 200 further monitors a $FiO_2$ level of the patient, graphs the oxygen saturation level of the blood in the patient as a function of the $FiO_2$ level and PEEP versus time, and then displays in the graph the oxygen saturation level of the blood in the patient as a function of the $FiO_2$ level and PEEP versus time. Accordingly, method 200 may further determine that either function is outside a preset threshold. If method 200 determines that the $FiO_2$ of the patient dropped prior to a drop in the oxygen saturation level of the blood in the patient, method 200 executes a $3^{rd}$ type $SpO_2$ alarm. Alternatively, if method 200 determines that the PEEP of the patient dropped prior to a drop in the oxygen saturation level of the blood in the patient, method 200 executes a $2^{nd}$ type $SpO_2$ alarm. In an another embodiment, if method 200 determines that the oxygen saturation level of the blood in the patient dropped independently of a drop in PEEP and/or $FiO_2$, then method 200 executes a first type oxygen saturation alarm. Further, the step of graphing the oxygen saturation level of the blood in the patient as a function of the $FiO_2$ level and PEEP versus time performed by method 200 can include converting PEEP data oxygen saturation level data, and $FiO_2$ data into a plotted graph and into displayable information.

Figure 3:
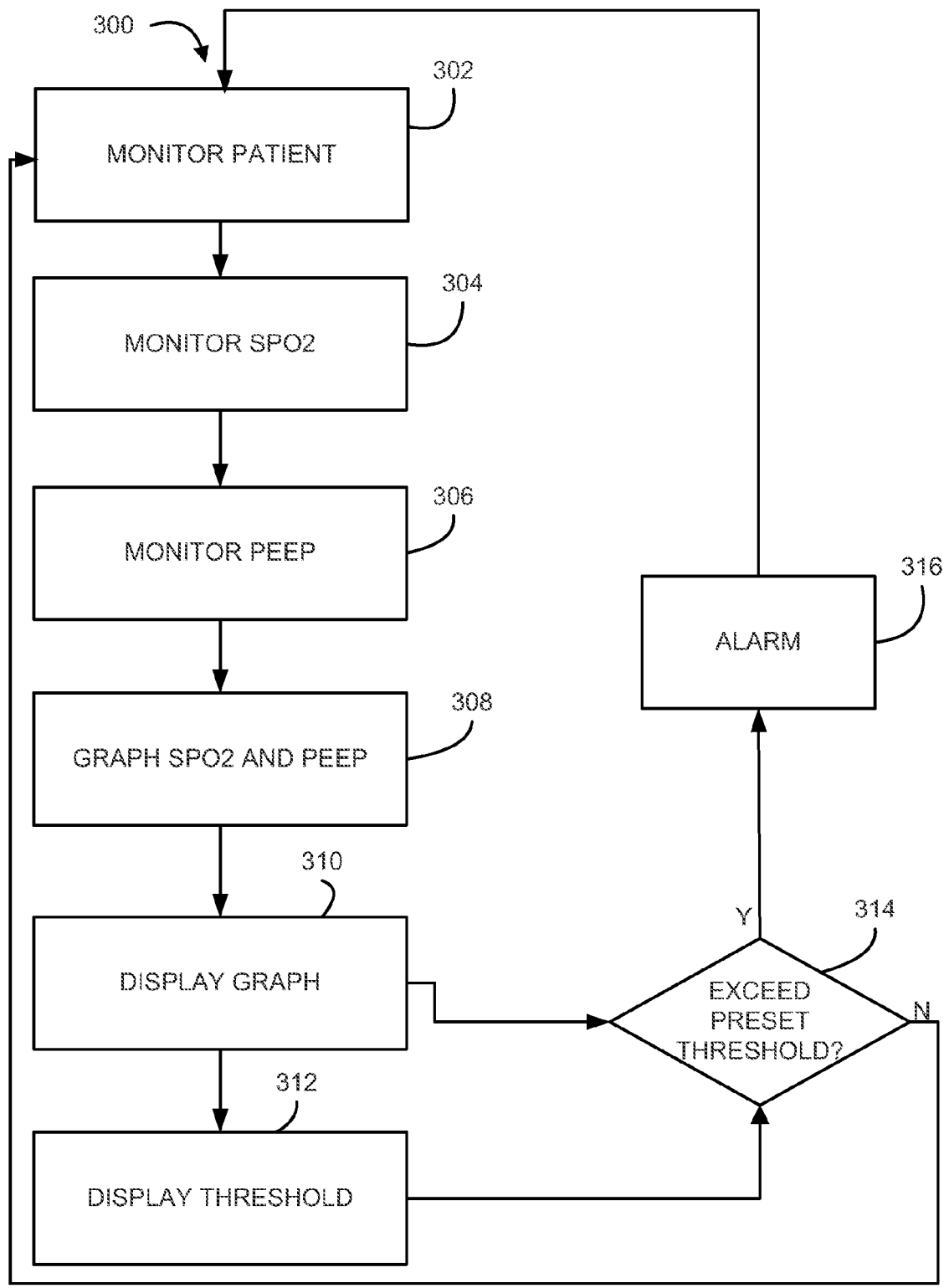
FIG. 3 illustrates an embodiment of a method for managing the ventilation of a patient being ventilated by a medical ventilator.

As illustrated in FIG. 3, an embodiment of a method 300 for managing the ventilation of a patient being ventilated by a medical ventilator is shown. Method 300 performs a patient monitoring operation 302. The patient monitoring operation 302 utilizes an oximeter to monitor the status of a patient during ventilation. The oximeter is operatively coupled to the controller of the ventilation system.

Next, method 300 performs a $SpO_2$ monitoring operation 304. The $SpO_2$ monitoring operation 304 determines the $SpO_2$ of the patient based on the results of the patient monitoring operation 302. The $SpO_2$ monitoring operation 304 can be performed by the oximeter or the ventilator. The oximeter or the ventilator utilizes oximeter sensor readings to monitor the $SpO_2$ of the patient.

Further, method 300 performs a PEEP monitoring operation 306. The PEEP monitoring operation 306 monitors the PEEP of the patient during ventilation. The PEEP monitoring operation 306 may monitor the PEEP of the patient with a flow and/or pressure sensor. The reading from the flow and/or pressure sensor may be utilized to monitor the PEEP of the patient.

Method 300 performs a graphing operation 308. The graphing operation 308 graphs $SpO_2$ and PEEP versus time. In one embodiment, graphing operation 308 graphs PEEP and $SpO_2$ as separate lines on one graph. In an alternative embodiment, graphing operation 308 calculates a function of PEEP and $SpO_2$ and graphs this number in one line versus time. The function of $SpO_2$ and PEEP may be the multiplication, addition, subtraction, ratio and/or any other mathematical relationship between the separate readings.

In one embodiment, the graphing operation 308 is performed by a controller. Further, the controller may include a graphing module for receiving and interpreting the PEEP and $SpO_2$ data to correctly graph this data versus time. The graphing operation 308 converts the PEEP and $SpO_2$ data into graphable information and displayable information.

Method 300 also performs a display operation 310. Display operation 310 displays the graph created by graphing step 308. The displaying operation 310 may display the graph on a display in the oximeter and/or ventilator. As illustrated in FIGS. 6 through 11, an embodiment of a graph of a function of $SpO_2$ and PEEP or separate $SpO_2$ and PEEP readings of a patient on a medical ventilator as displayed on a display screen is shown.

Next, method 300 performs a preset threshold display operation 312. The preset threshold display operation 312 displays at least one preset threshold on the graph displayed by display operation 310. The preset threshold provides the patient, operator, and/or medical care giver with a quick reference point to determine the status of the patient during ventilation. In an embodiment, preset threshold display operation 312 displays an upper and a lower preset threshold limit on the graph. Preset threshold display operation 312 may depict a preset threshold with color, symbols, lines, light, and/or text. The preset threshold may be preset by the operator, configured into the ventilator based on the ventilator settings, and/or selected by the operator.

Further, method 300 performs a preset threshold determination operation 314. The preset threshold determination operation 314 determines if PEEP, $SpO_2$, and/or a function of PEEP and $SpO_2$ preset threshold was exceeded. If preset threshold determination operation 314 determines that a preset threshold was exceeded, preset threshold determination operation 314 has method 300 perform an alarm operation 316. If preset threshold determination operation 314 determines that a preset threshold was not exceeded, preset threshold determination operation 314 has method 300 perform patient monitoring operation 302 again.

Method 300 performs an alarm operation 316. The alarm operation 316 executes an alarm to notify the operator that a preset threshold has been exceeded. The alarm may be any visual and/or audio cue. After performing alarm operation 316, method 300 performs patient monitoring operation 302 again.

Figure 4:
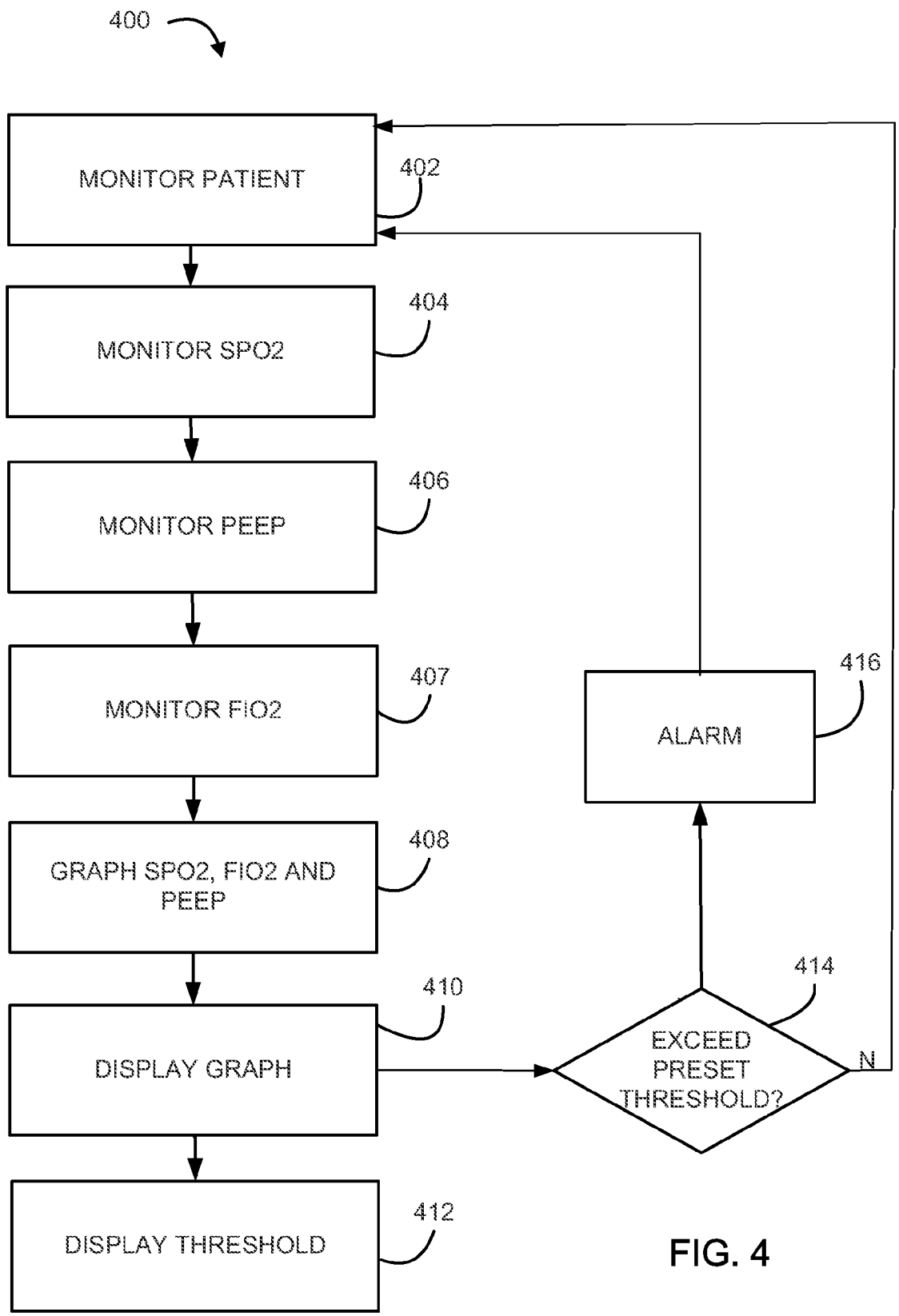
FIG. 4 illustrates an embodiment of a method for managing the ventilation of a patient being ventilated by a medical ventilator.

As illustrated in FIG. 4, an embodiment of a method 400 for managing the ventilation of a patient being ventilated by a medical ventilator is shown. Method 400 performs a patient monitoring operation 402. The patient monitoring operation 402 utilizes an oximeter to monitor the status of a patient during ventilation. The oximeter is operatively coupled to the controller of the ventilation system.

Next, method 400 performs a $SpO_2$ monitoring operation 404. The $SpO_2$ monitoring operation 404 determines the $SpO_2$ of the patient based on the results of the patient monitoring operation 402. The $SpO_2$ monitoring operation 404 can be performed by the oximeter and/or the ventilator. The oximeter and/or the ventilator utilize oximeter sensor readings to monitor the $SpO_2$ of the patient.

Further, method 400 performs a PEEP monitoring operation 406. The PEEP monitoring operation 406 monitors the PEEP of the patient during ventilation. The PEEP monitoring operation 406 may monitor the PEEP of the patient with a flow and/or pressure sensor. The reading from the flow and/or pressure sensor may be utilized to monitor the PEEP of the patient.

Further, method 400 performs a $FiO_2$ monitoring operation 407. The $FiO_2$ monitoring operation 407 monitors the $FiO_2$ of the patient during ventilation. The $FiO_2$ monitoring operation 407 may monitor the $FiO_2$ of the patient with a gas sensor and/or a flow and/or pressure sensor. The reading from the gas sensor may be utilized to monitor the $FiO_2$ of the patient.

Method 400 performs a graphing operation 408. The graphing operation 408 graphs $SpO_2$, $FiO_2$, and PEEP versus time. In one embodiment, graphing operation 408 graphs PEEP, $FiO_2$, and $SpO_2$ as separate lines on one graph. In an alternative embodiment, graphing operation 408 calculates a function of PEEP, $FiO_2$, and $SpO_2$ and graphs this number in one line versus time. The function of $FiO_2$, $SpO_2$ and PEEP may be the multiplication, addition, subtraction, ratio and/or any other mathematical relationship between the separate readings.

In one embodiment, the graphing operation 408 is performed by a controller. The controller may be located in the oximeter and/or the ventilator. Further, the controller may include a graphing module for receiving and interpreting the PEEP, $FiO_2$, and $SpO_2$ data to correctly graph this data versus time. The graphing operation 408 converts the PEEP, $FiO_2$, and $SpO_2$ data into graphable information and displayable information.

Figure 12:
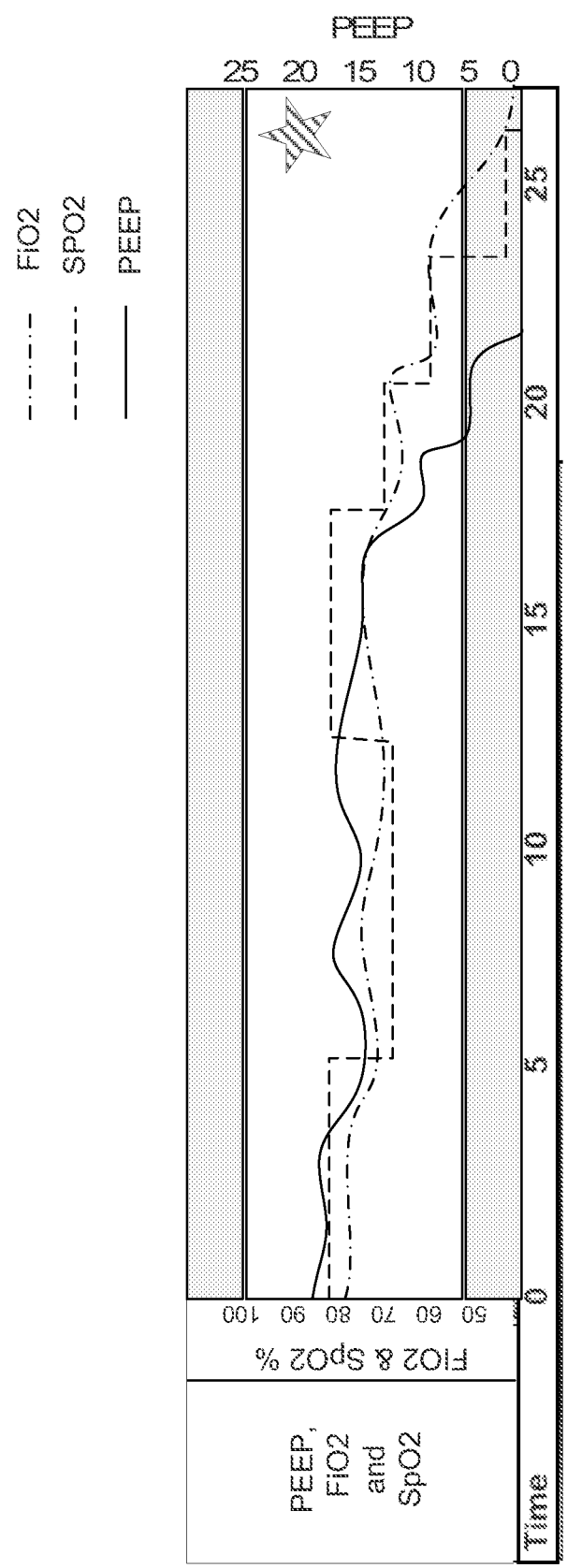
FIG. 12 illustrates an embodiment of a graph of a $SpO_2$, $FiO_2$, and PEEP of a patient on a medical ventilator versus time as displayed on a display screen.
Figure 13:
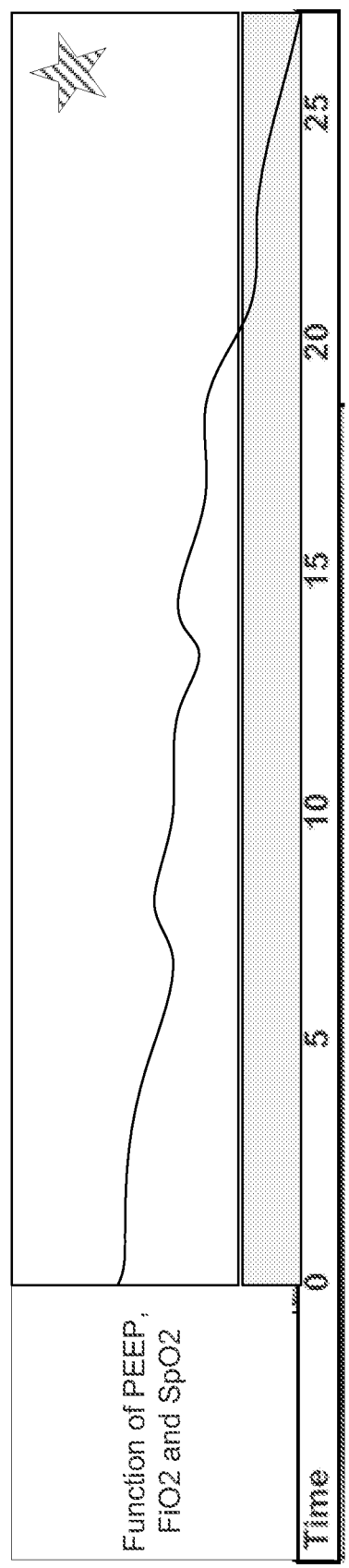
FIG. 13 illustrates an embodiment of a graph of a function of $SpO_2$, $FiO_2$, and PEEP of a patient on a medical ventilator versus time as displayed on a display screen.

Method 400 also performs a display operation 410. Display operation 410 displays the graph created by graphing step 408. The displaying operation 410 may display the graph on a display in the oximeter and/or ventilator. As illustrated in FIGS. 12 and 13, an embodiment of a graph of a function of $FiO_2$, $SpO_2$ and PEEP or separate $SpO_2$, $FiO_2$, and PEEP readings of a patient on a medical ventilator versus time as displayed on a display screen is shown.

Next, method 400 performs a preset threshold display operation 412. The preset threshold display operation 412 displays at least one preset threshold on the graph displayed by display operation 408. The preset threshold provides the patient, operator, and/or medical care giver with a quick reference point to determine the status of the patient during ventilation. In an embodiment, preset threshold display operation 412 displays an upper and a lower preset threshold limit on the graph. Preset threshold display operation 412 may depict a preset threshold with color, symbols, lines, light, and/or text. The preset threshold may be preset by the operator, configured into the ventilator based on the ventilator settings, and/or selected by the operator.

Further, method 400 performs a preset threshold determination operation 414. The preset threshold determination operation 414 determines if a PEEP, $FiO_2$, $SpO_2$, and/or a function of PEEP, $FiO_2$, and $SpO_2$ preset threshold was exceeded. If preset threshold determination operation 414 determines that a preset threshold was exceeded, preset threshold determination operation 414 has method 400 perform an alarm operation 416. If preset threshold determination operation 414 determines that a preset threshold was not exceeded, preset threshold determination operation 414 has method 400 perform patient monitoring operation 402 again.

Method 400 performs an alarm operation 416. The alarm operation 416 executes an alarm to notify the operator that a preset threshold has been exceeded. The alarm may be any visual and/or audio cue. After performing alarm operation 416, method 400 performs patient monitoring operation 402 again.

Figure 5:
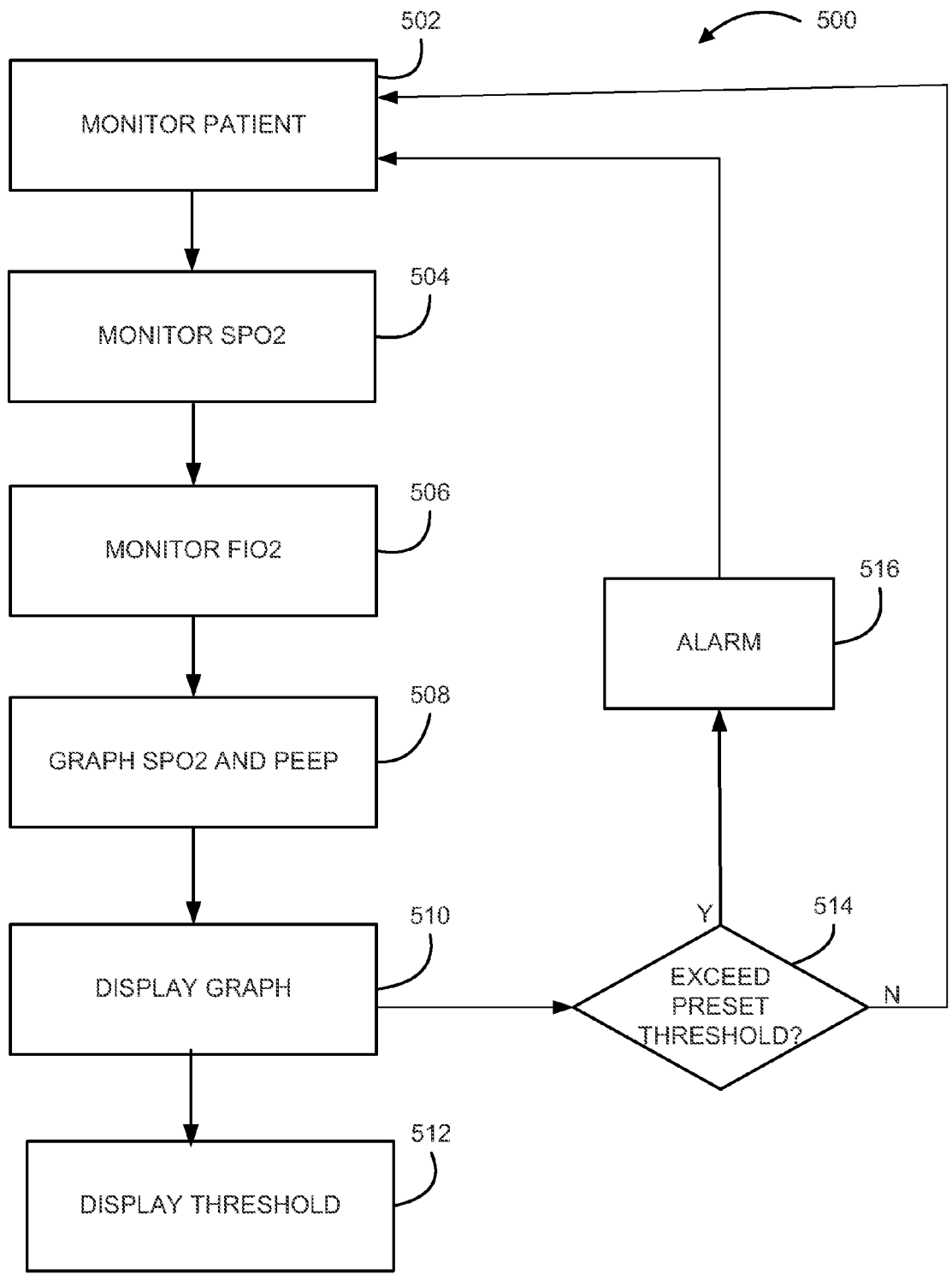
FIG. 5 illustrates an embodiment of a method for managing the ventilation of a patient being ventilated by a medical ventilator.
Figure 6:
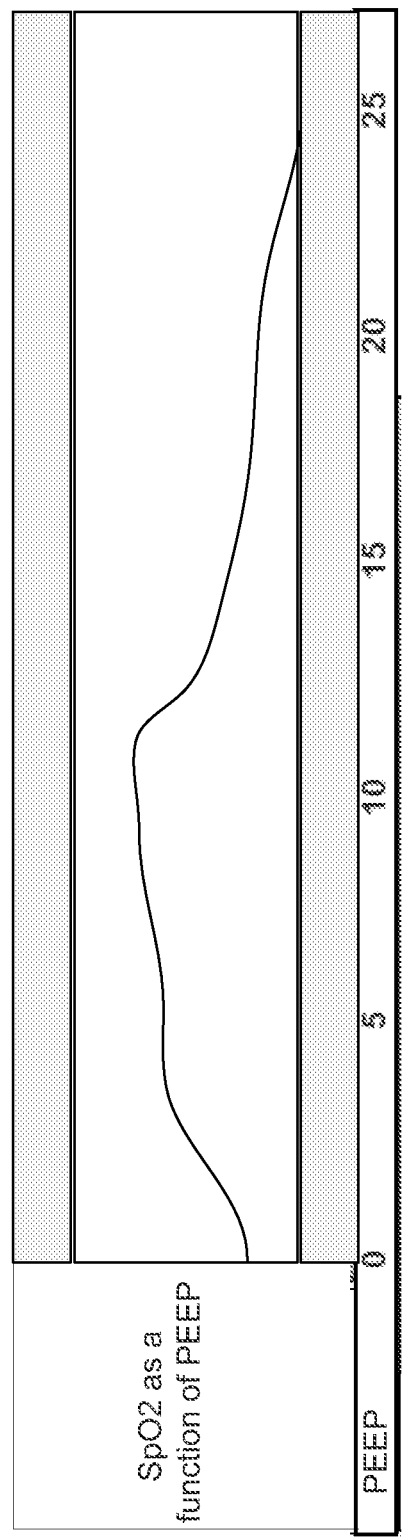
FIG. 6 illustrates an embodiment of a graph of $SpO_2$ as a function of PEEP as displayed on a display screen.

As illustrated in FIG. 5, an embodiment of a method 500 for managing the ventilation of a patient being ventilated by a medical ventilator is shown. Method 500 performs a patient monitoring operation 502. The patient monitoring operation 502 utilizes an oximeter to monitor the status of a patient during ventilation. The oximeter is operatively coupled to the controller of the ventilation system.

Next, method 500 performs a $SpO_2$ monitoring operation 504. The $SpO_2$ monitoring operation 504 determines the $SpO_2$ of the patient based on the data gathered by the patient monitoring operation 502. The $SpO_2$ monitoring operation 504 can be performed by the oximeter or the ventilator. The oximeter or the ventilation utilizes oximeter sensor readings to monitor the $SpO_2$ of the patient.

Further, method 500 performs a $FiO_2$ monitoring operation 506. The $FiO_2$ monitoring operation 506 monitors the $FiO_2$ of the patient during ventilation. The $FiO_2$ monitoring operation 506 may monitor the $FiO_2$ of the patient with a gas sensor and/or a flow and/or pressure sensor. The reading from the gas sensor may be utilized to monitor the $FiO_2$ of the patient.

Method 500 performs a graphing operation 508. The graphing operation 508 graphs $SpO_2$ and $FiO_2$ versus time. In one embodiment, graphing operation 508 graphs $FiO_2$ and $SpO_2$ as separate lines on one graph. In an alternative embodiment, graphing operation 508 calculates a function of $FiO_2$ and $SpO_2$ and graphs this number in one line versus time. The function of $SpO_2$ and $FiO_2$ may be the multiplication, addition, subtraction, and/or ratio of the separate readings.

In one embodiment, the graphing operation 508 is performed by a controller. The controller may be located in the oximeter and/or the ventilator. Further, the controller may include a graphing module for receiving and interpreting the raw $FiO_2$ and $SpO_2$ data to correctly graph this data versus time. The graphing operation 508 converts the raw $FiO_2$ and $SpO_2$ data into graphable information and displayable information.

Method 500 also performs a display operation 510. Display operation 510 displays the graph created by graphing step 508. The displaying operation 510 may display the graph on a display in the oximeter and/or ventilator.

Next, method 500 performs a preset threshold display operation 512. The preset threshold display operation 512 displays at least one preset threshold on the graph displayed by display operation 508. The preset threshold provides the patient, operator, and/or medical care giver with a quick reference point to determine the status of the patient during ventilation. In an embodiment, preset threshold display operation 512 displays an upper and a lower preset threshold limit on the graph. Preset threshold display operation 512 may depict a preset threshold with color, symbols, lines, light, and/or text. The preset threshold may be preset by the operator, configured into the ventilator based on the ventilator settings, and/or selected by the operator.

Further, method 500 performs a preset threshold determination operation 514. The preset threshold determination operation 514 determines if a $FiO_2$, $SpO_2$, and/or a function of $FiO_2$ and $SpO_2$ preset threshold was exceeded. If preset threshold determination operation 514 determines that a preset threshold was exceeded, preset threshold determination operation 514 has method 500 perform an alarm operation 516. If preset threshold determination operation 514 determines that a preset threshold was not exceeded, preset threshold determination operation 514 has method 500 perform patient monitoring operation 502 again.

Method 500 performs an alarm operation 516. The alarm operation 516 executes an alarm to notify the operator that a preset threshold has been exceeded. The alarm may be any visual and/or audio cue. After performing alarm operation 516, method 500 performs patient monitoring operation 502 again.

In alternative embodiment, a computer-readable medium having computer-executable instructions for performing a method for managing the ventilation of a patient being ventilated by a medical ventilator is disclosed. The method includes repeatedly performing the steps disclosed in method 200, method 300, method 400, or method 500.

In another embodiment, a medical ventilator system is disclosed. The medical ventilator includes means for repeatedly monitoring a patient during ventilation with an oximeter, means for repeatedly monitoring an oxygen saturation level of blood in the patient during ventilation, means for repeatedly monitoring a PEEP level of the patient, means for repeatedly graphing the oxygen saturation level of the blood in the patient as a function of the PEEP level versus time, and means for repeatedly displaying a graph of the function versus time. In one embodiment, the means for the medical ventilator system are all illustrated in FIG. 1 and description above in the description of FIG. 1. However, the means described above for FIG. 1 and illustrated in FIG. 1 are exemplary only and are not meant to be limiting.

EXAMPLE 1

The following are embodiments of graphs that can be displayed on a display screen of a medical ventilator or an oximeter that graphs PEEP and $SpO_2$ versus time.

Figure 7:
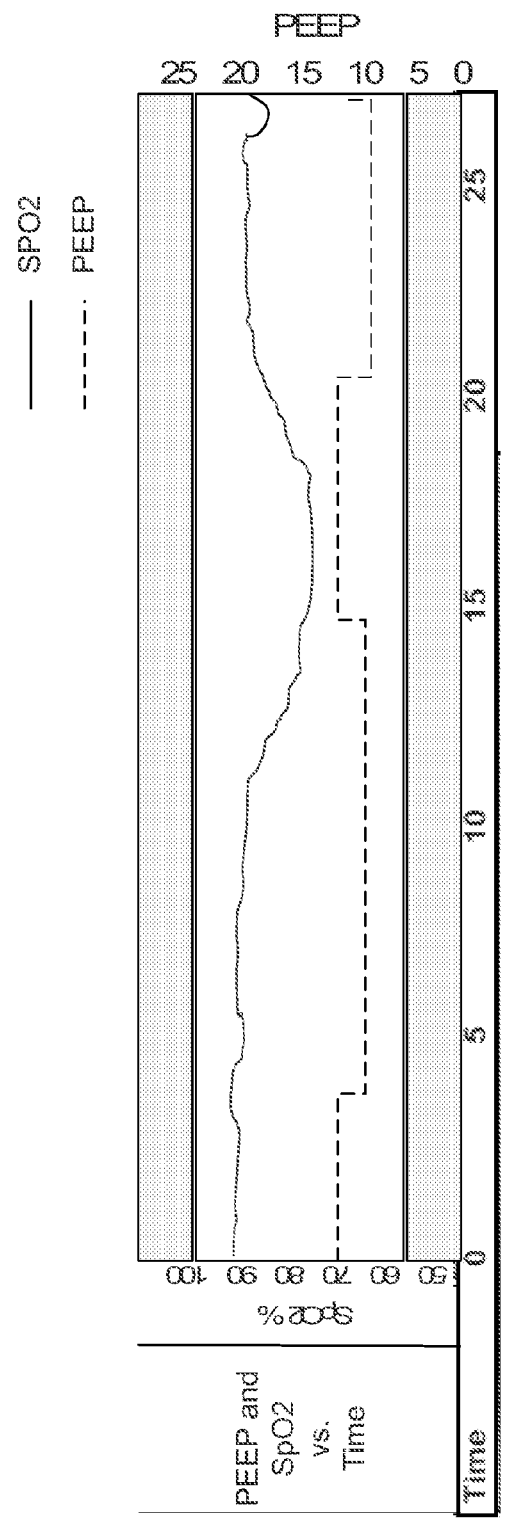
FIG. 7 illustrates an embodiment of a graph of $SpO_2$ and PEEP of a patient on a medical ventilator versus time as displayed on a display screen.
Figure 8:
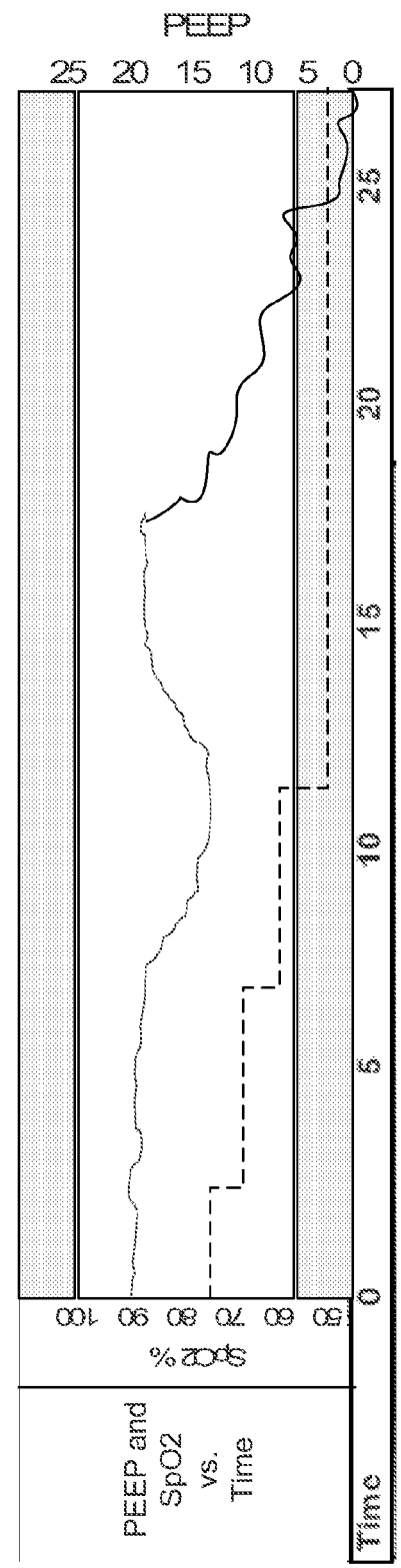
FIG. 8 illustrates an embodiment of a graph of $SpO_2$ and PEEP of a patient on a medical ventilator versus time as displayed on a display screen.
Figure 11:
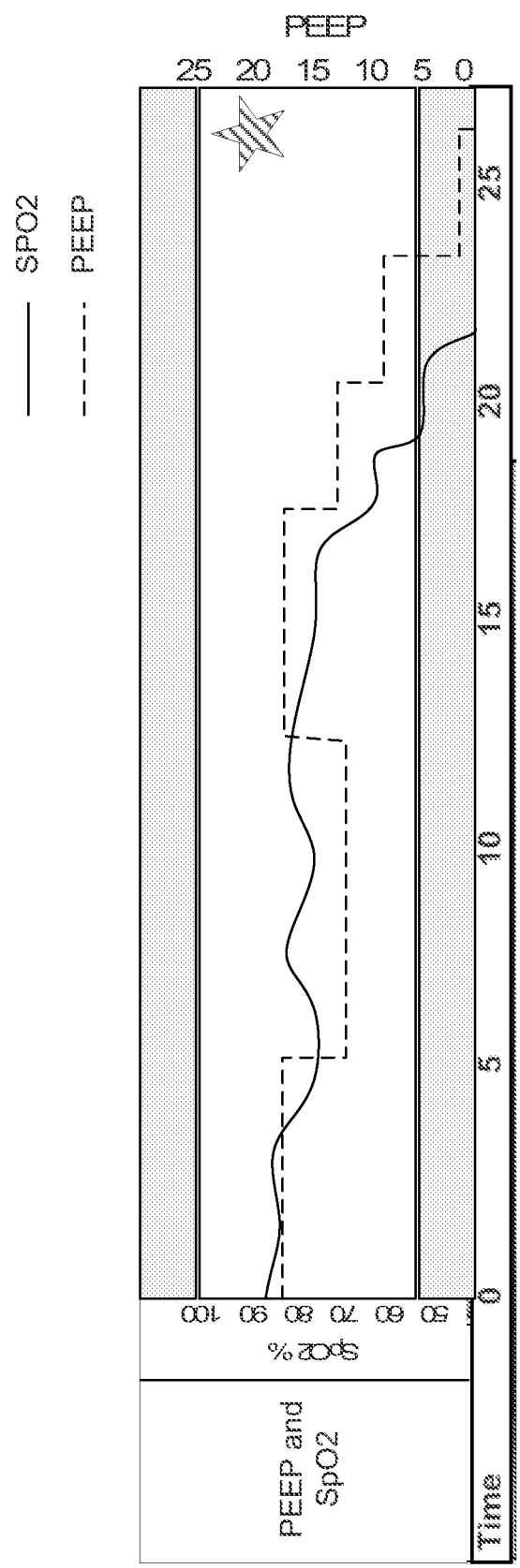
FIG. 11 illustrates an embodiment of a graph of a function of $SpO_2$ and PEEP of a patient on a medical ventilator versus time as displayed on a display screen.

The following are embodiments of graphs that depict PEEP and $SpO_2$ as separate lines versus time that can be displayed on a display screen. A display may show a graph with an upper and lower preset threshold for two separate lines depicting the patient's $SpO_2$ and PEEP during ventilation versus time in seconds as illustrated in FIGS. 7, 8, and 11. As shown in FIG. 7, both PEEP and $SpO_2$ remain within the upper and lower preset thresholds depicted by the shaded areas. FIG. 8 illustrates a preset threshold that was exceeded first by a drop in PEEP and followed by a drop in $SpO_2$. The appropriate scales for PEEP and $SpO_2$ may be displayed in any conventional manner.

FIG. 11 illustrates a preset threshold that was exceeded first by a drop in $SpO_2$ and then followed by a drop in PEEP. FIG. 11 further illustrates a visual alarm icon that indicates that a preset threshold was exceeded first by a drop in $SpO_2$ followed by a drop in PEEP. As illustrated in FIG. 11, the visual alarm cue is a colored star that flashes in the corner of the graph. This alarm is exemplary only and does not limit the disclosure.

The following are embodiments of graphs that depict a function of $SpO_2$ and PEEP versus time that can be displayed on display screen. The function of $SpO_2$ and PEEP may be the multiplication, addition, subtraction, ratio, and/or any other mathematical relationship between the parameters. For example, in an embodiment, PEEP and $SpO_2$ for any given period (e.g., for each monitoring cycle of 5 ms or for a group of monitoring cycles) are multiplied resulting in a graph of $P_{PEEP}*O_2\%$ v. time. However, any function of PEEP and $SpO_2$ of clinical value may be used. A display may show a graph with an upper and lower preset threshold for the function of the patient's $SpO_2$ and PEEP during ventilation versus time in seconds.

In an alternative example, a display may show a graph with only a lower preset threshold and one line depicting the function of the patient's $SpO_2$ and PEEP during ventilation versus time in seconds as illustrated in FIGS. 9 and 10. The lower preset threshold is the shaded area in the graphs illustrated in FIGS. 9 and 10. FIGS. 9 and 10 further illustrate visual alarm icons that indicate that a preset threshold was exceeded by a drop in $SpO_2$ independently of a change in PEEP or was exceeded first by a drop in PEEP followed by a drop in $SpO_2$. As illustrated in FIG. 11, the visual alarm icon is a colored star that flashes in the corner of the graph when a preset threshold is exceeded by a drop in $SpO_2$ independently of a change in PEEP. As illustrated in FIG. 9, the visual alarm icon is a colored circle that flashes in the corner of the graph when the preset threshold was exceeded first by a drop in PEEP followed by a drop in $SpO_2$. These alarms are exemplary only and do not limit the disclosure.

The following are embodiments of graphs that can be displayed on a display screen of a medical ventilator or an oximeter that graphs PEEP, $FiO_2$ and $SpO_2$ versus time.

The following is an embodiment of a graph that depicts PEEP, $FiO_2$ and $SpO_2$ as separate lines versus time that can be displayed on a display screen. A display may show a graph with an upper and lower preset threshold for three separate lines depicting the patient's $SpO_2$, $FiO_2$, and PEEP during ventilation versus time in seconds as illustrated in FIG. 12. As shown in FIG. 12 a preset threshold that was exceeded first by a drop in PEEP and followed by a drop in $SpO_2$. The appropriate scales for PEEP, $FiO_2$, and $SpO_2$ may be displayed in any conventional manner.

The following is an embodiment of a graph that depicts a function of $SpO_2$, PEEP, and $FiO_2$ versus time that can be displayed on a display screen. The function of $SpO_2$, PEEP and $FiO_2$ may be the multiplication, addition, subtraction, ratio, and/or any other mathematical relationship between the parameters. For example, in an embodiment, PEEP, $FiO_2$, and $SpO_2$ for any given period (e.g., for each monitoring cycle of 5 ms or for a group of monitoring cycles) are multiplied resulting in a graph of $P_{FiO2}*P_{PEEP}*O_2\%$ v. time. However, any function of PEEP, $FiO_2$, and $SpO_2$ of clinical value may be used. A display may show a graph with an upper and/or lower preset threshold for the function of the patient's $SpO_2$, $FiO_2$, and PEEP during ventilation versus time in seconds. FIG. 13 illustrates a graph displaying a lower preset threshold for the function of the patient's $SpO_2$, $FiO_2$, and PEEP during ventilation versus time in seconds. As shown in FIG. 4, the function of PEEP and $SpO_2$ exceeds the lower preset threshold depicted by the shaded areas activating an alarm icon (i.e. a colored star icon). The displayed alarm is exemplary only and does not limit the disclosure.

Numerous other changes may be made which will readily suggest themselves to those skilled in the art and which are encompassed in the spirit of the disclosure and as defined in the appended claims. For example, in the embodiments of the methods described herein various operations and steps could be combined into a single operation (e.g., a single monitoring operation) or the operations could be performed in a different order or as parallel operations. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method for managing ventilation of a patient being ventilated by a medical ventilator, the method comprising:
monitoring a patient during ventilation with an oximeter;
monitoring an oxygen saturation level of blood in the patient during ventilation;
monitoring a PEEP level of the patient;
graphing a function of the oxygen saturation level of the blood of and the PEEP level versus time;
displaying a graph of the function versus time; issuing a first alarm if the function is outside of a preset threshold, a drop in the oxygen saturation level of the blood is detected, and the PEEP level does not change; and
issuing a second alarm if the function is outside of the preset threshold and the drop in the oxygen saturation level of the blood occurred after the PEEP level dropped.

2. The method of claim 1, wherein the graph is displayed by an oximeter display.

3. The method of claim 1, wherein the graph is displayed by a ventilator display.

4. The method of claim 1, further comprising displaying at least one preset threshold on the graph.

5. The method of claim 1, wherein the step of graphing the function comprises converting raw PEEP data and raw oxygen saturation level data into a plotted graph and into displayable information.

6. The method of claim 1, further comprising:
monitoring a fractional inspired oxygen level of the patient;
graphing a function of the oxygen saturation level of the blood and the fractional inspired oxygen level versus time; and
displaying on the graph the function of the oxygen saturation level of the blood and the fractional inspired oxygen level versus time.

7. The method of claim 1, wherein the step of issuing the first alarm includes displaying the first alarm.

8. The method of claim 7, wherein the step of displaying the first alarm includes displaying the first alarm on the graph.

9. The method of claim 7, wherein the step of displaying the first alarm includes displaying the first alarm as an icon.

10. The method of claim 1, wherein the step of issuing the first alarm includes issuing an audio notification.

11. The method of claim 4, wherein the step of displaying the at least one preset threshold on the graph includes displaying the at least one preset threshold as a shaded area on the graph.

12. The method of claim 1, wherein the function is the oxygen saturation level of blood multiplied by the PEEP level for a given period.

13. The method of claim 1, further comprising:
issuing a third alarm if the function is outside of the preset threshold and the drop in the oxygen saturation level of the blood occurred before the PEEP level dropped.

14. A non-transitory computer-readable medium having computer-executable instructions for performing a method for managing ventilation of a patient being ventilated by a medical ventilator, the method comprising:
repeatedly monitoring a patient during ventilation with an oximeter;
repeatedly monitoring an oxygen saturation level of blood in the patient during ventilation;
repeatedly monitoring a PEEP level of the patient;
repeatedly graphing a mathematical relationship of the oxygen saturation level of the blood and the PEEP level versus time;
repeatedly displaying a graph of the mathematical relationship versus time;
repeatedly issuing a first alarm if the mathematical relationship is outside of a preset threshold, a drop in the oxygen saturation level of the blood is detected, and the PEEP level does not change; and
repeatedly issuing a second alarm if the mathematical relationship is outside of the preset threshold and the drop in the oxygen saturation level of the blood occurred after a drop in the PEEP level.

15. The method of claim 14, further comprising:
repeatedly issuing a third alarm if the mathematical relationship is outside of the preset threshold and the drop in the oxygen saturation level of the blood occurred before the drop in the PEEP level.

16. A medical ventilator system, comprising:
means for monitoring a patient during ventilation with an oximeter;
means for monitoring an oxygen saturation level of blood in the patient during ventilation;
means for monitoring a PEEP level of the patient;
means for graphing a mathematical relationship of the oxygen saturation level of the blood and the PEEP level versus time;
means for displaying a graph of the mathematical relationship versus time;
means for determining that the mathematical relationship is outside a preset threshold;
means for determining that the PEEP level of the patient dropped prior to a drop in the oxygen saturation level of the blood in the patient, determining that the oxygen saturation level of the blood in the patient dropped prior to a drop in the PEEP level, and determining the drop in the oxygen saturation level of the blood when the PEEP level does not change;
means for issuing a first alarm if the mathematical relationship is outside of the preset threshold, the drop in the oxygen saturation level of the blood is detected, and the PEEP level does not change; and
means for issuing a second alarm if the mathematical relationship is outside of the preset threshold and the drop in the oxygen saturation level of the blood occurred after the PEEP level dropped.

17. The method of claim 16, further comprising:
means for issuing a third alarm if the mathematical relationship is outside of the preset threshold and the drop in the oxygen saturation level of the blood occurred before the PEEP level dropped.

* * * * *